United States Patent [19]

van Zuilichem

[11] Patent Number: 4,930,524

[45] Date of Patent: Jun. 5, 1990

[54] DEVICE FOR LUMBAR TRACTION IN PHYSIOTHERAPY

[76] Inventor: Hendrikus C. W. van Zuilichem, van Zuilichem & Partners, Equipment Manual Therapy, P.O. Box 46, 4750 AA Oud Gastel, Netherlands

[21] Appl. No.: 246,075

[22] Filed: Sep. 19, 1988

[51] Int. Cl.[5] .......................... A61F 13/00; A61F 5/04; A61H 1/02

[52] U.S. Cl. .................................. 128/876; 128/84 C; 128/75

[58] Field of Search ................. 128/876, 84 C, 85, 75, 128/870, 87 B, 80 R, 869, 875; 5/80, 444; 269/322, 326

[56] References Cited

U.S. PATENT DOCUMENTS

| | | | |
|---|---|---|---|
| 826,648 | 7/1906 | Challenger | 128/876 |
| 2,191,097 | 2/1940 | Morrison | 128/85 |
| 2,215,454 | 9/1940 | Condit | 128/870 |
| 2,638,091 | 5/1953 | Varco | 128/75 |
| 2,853,999 | 9/1958 | Risser | 128/84 C |
| 3,153,411 | 10/1964 | Unks | 128/75 |
| 3,522,802 | 8/1970 | Morton | 128/75 |
| 3,535,719 | 10/1970 | Murcott | 128/876 |
| 3,734,088 | 5/1973 | Tucker, Jr. | 128/75 |
| 4,466,427 | 8/1984 | Granberg | 128/75 |
| 4,579,109 | 4/1986 | Lundblad | 128/75 |
| 4,602,619 | 7/1986 | Wolf | 128/69 |
| 4,641,637 | 2/1987 | Rosen | 128/84 C |
| 4,664,099 | 5/1987 | Pearl, Jr. | 128/84 C |
| 4,674,484 | 6/1987 | Kott | 128/69 |

*Primary Examiner*—Robert A. Hafer
*Assistant Examiner*—Michael Brown
*Attorney, Agent, or Firm*—Horst M. Kasper

[57] ABSTRACT

A device for lumbar traction in physiotherapists practice with a thoracal fixation belt (1) with widened thoracal belt part (2), and extension piece (3), a longitudinal traction belt (4), pelvical girdle (5), abdominal belt (6), handle clamps (7), traction girdle (8), connection rod (9), traction rope with optional pulley block (10), and body adjusting wedge (11), forming a unit to alleviate deficiencies of the human lumbar and thoracal parts of the intervertebral system.

6 Claims, 2 Drawing Sheets

DEVICE FOR LUMBAR TRACTION IN PHYSIOTHERAPY

Figure 1:
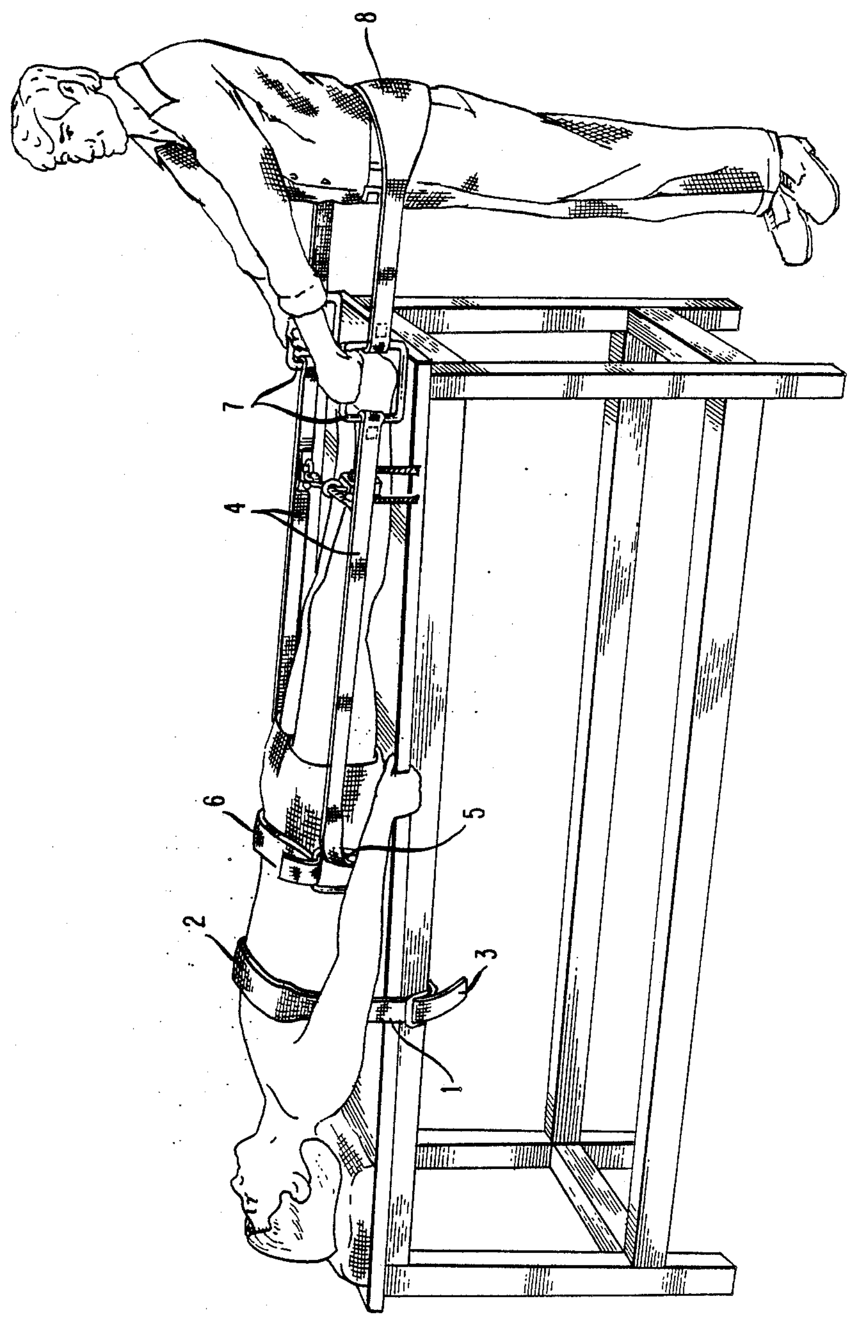

The present invention relates to a device for applying lumbar traction to patients, who are suffering of diseases of the spinal column. With a unit according to this invention painful deficiencies of the lumbal and the thoracal parts of the skeleton can be alleviated by the physiotherapist. Manual therapy methods as a remedy for these infirmities are well-known, but background art has some disadvantages. The manual therapy causes severe physical efforts for the therapist, and the reproducibility in view of a systematic approach is difficult to obtain in an equal manner.

According to the present invention means have been developed, which constitute a unit for several physical traction systems and for use in several directions, which can be adapted to the specific needs of the patient in question. The deflections or deviations of the spinal column and of the joint articular parts have been described in Kremer, "Intervertebral Disc Diseases", Ed. Thieme, Göttingen-New York (1980).

The lumbar traction unit according to the present invention is an expedient means to perform tractions in several dimensional directions in a most convenient and comfortable way, such that possibilities for the patient and purposes of the therapist are met at any kind, in the physiological positions of lordosis and cyphosis, segmental treatments included.

The unit can be used upon a standard massage reclining table, which can be adjusted in height, accomodated to the therapist.

A particular advantage is the adjustability of all parts, in such a manner, that these can be accomodated to any bodily constitution and condition. The fixation of the body by belts and girdles is optimal.

The lumbar traction unit for physiotherapeutical treatment of spinal column complaints is a specific compilation of fixation girdles and traction belts, with adjustment parts, comprising a thoracal fixation belt having a widened part to be laid upon the lower part of the thorax, and having an adjustable extension piece to be fastened underneath the table with a clasp, in such a manner that it is prevented from slipping off, and a pelvic girdle with an abdominal belt, connected with a pair of longitudinal traction belts, the latter being connected with each other by a connection rod, bearing in its middle a traction rope with optional pulley block, and having in its prolongation a traction girdle, affixed at the junction with the longitudinal traction belt by means of a pair of handle clamps, and the unit is completed by a loose body-adjusting wedge, which is to be positioned between the longitudinal traction belts, as a support under the spine, such that somewhat spacing remains between the lower edge of said wedge on the table and the spine of the patient.

The treatment with the lumbar traction unit is carried out as follows:

A thoracal fixation belt is laid around the lower part of the thorax and affixed underneath the table.

The widened part must be positioned upon the thorax. The extension piece of this belt allows to adjust the grade of fixation.

The pelvical girdle is laid under the pelvis and an abdominal belt is laid over the abdomen.

A pair of longitudinal traction belts connected therewith extends along the thighs and the legs and these are connected with each other by a connection rod, while in their prolongation these are connected with the therapists' traction girdle by means of handle clamps, which allow manual traction. The traction girdle is slung around the hips of the therapist. The traction rope at the connection rod accomodates manipulation. The traction girdle allows application of traction force.

Optional a pulley block with servo motor drive can be connected with the traction rope to allow a slow and controlled mechanical traction, until a predetermined degree of traction is reached and can be maintained during a short period.

For the purpose of a low-thoracal and middle-thoracal traction treatment, the body adjusting wedge can be positioned between the thoracal spine part and the table between the longitudinal traction belts.

All connections for adjustment to correct anatomic sizes can be made by means of tangle fastening twill strings, whereof two string ends tangle with each other. Fixation by means of clasps is also possible.

By means of a combination of fixation adjustment, position of the body and control of lumbar traction in appropriate dimensions, the structure of the spinal system can be influenced and improved. The patient can be laid in spinal, abdominal and in lateral position. The traction can be applied in symmetrical or in asymmetrical manner.

The device according to the present invention is further elucidated on the basis of the enclosed schematic drawings.

In these drawings, FIG. 1 shows the position of the patient provided with both parts of the present lumbar traction device.

Figures 2, 3, 4:
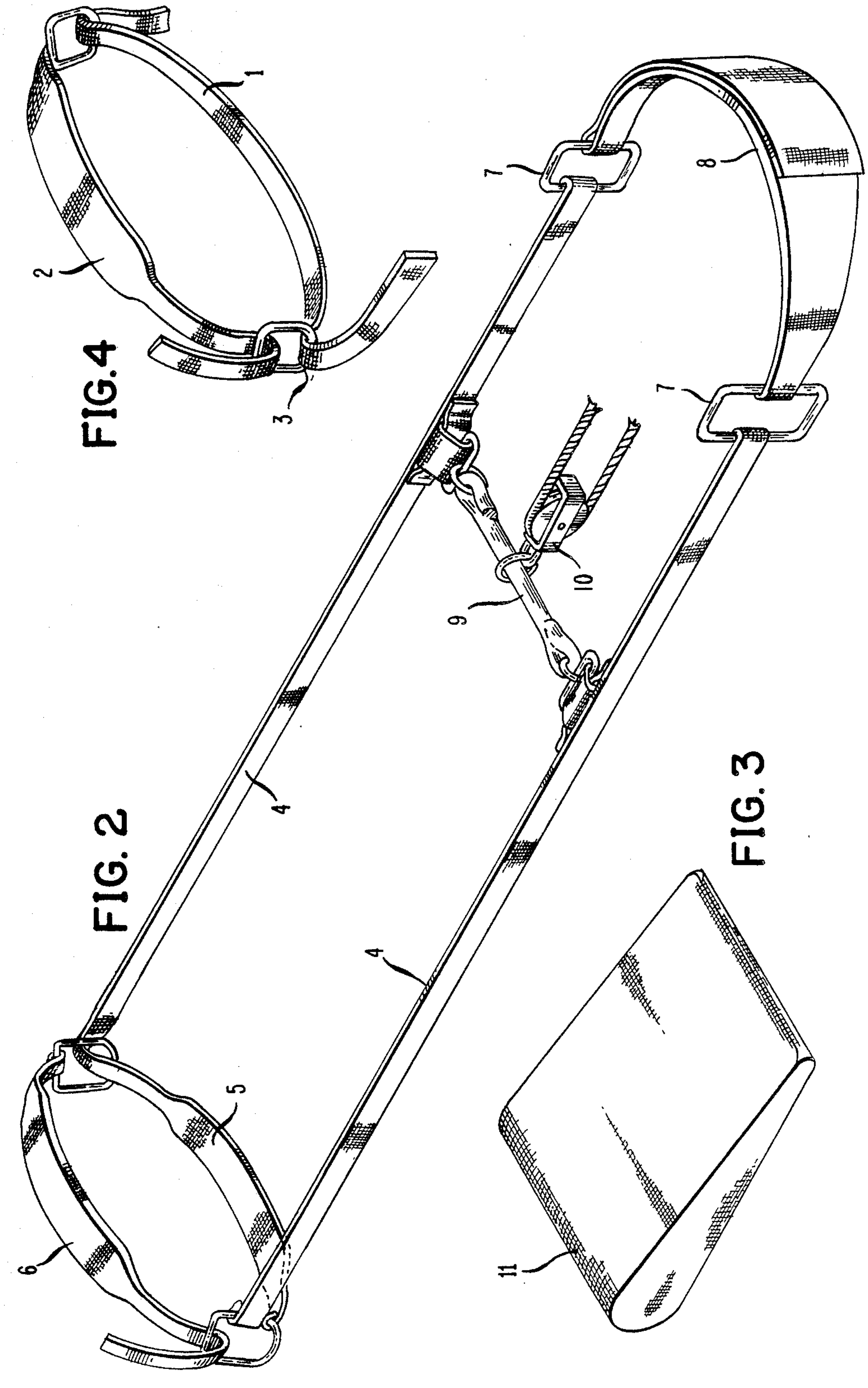

FIG. 2 shows the substantial parts of the device.

The thorax is held in position by means of the thoracal fixation belt (1) with its widened thoracal belt part (2) around the front side of the patient body, while the end of the extension piece (3) of that belt is visible underneath the table.

The pelvical girdle (5) is laid under the patients pelvis, such that the connected abdominal belt (6) is positioned around the upper pelvis and over the lower abdomen.

The pelvical girdle (5) and the abdominal belt (6) are connected to the pair of longitudinal traction belts (4), which are laid along the thighs and the legs, and said belts are connected by the connection rod (9), while adjacent to these junctions a connection is made with handle clamps (7) and the traction girdle (8), the latter forming a sling to be laid around the body of the therapist.

In the middle of the connection rod (9) is a traction rope, with a pulley block (10), which can be used optionally, driven by a servo motor drive to deliver a predetermined traction.

FIG. 3 shows the body adjusting wedge (11), which is put under the spine of the patient, in order to make a low-thoracal or middle-thoracal traction manipulation. This wedge (11) is placed with its lower edge towards the upper part of the spine and it is secured at both sides to the inner edge of the longitudinal traction belt (4). An air space between the table, the edge of the body adjusting wedge (11) and the back of the patient is obtained, which is necessary for traction at the lower part of the thorax.

During the traction the patient can accomodate to the fixation of the thoracal fixation belt and of the pelvical girdle, because he can reach the ends of the extending piece (3) and (6).

The pelvical girdle (5) and the abdominal belt (6) are drawn tight like breeches, by means of the extending ends.

The therapist is standing at the foot-end of the table, steps into the traction girdle (8) and places the pelvical part of same upon his sacrum. The traction is effected by means of the body weight of the therapist, controlling with his hands at both the handle clamps (7).

The length of the longitudinal traction belts (4) is variable by shifting the handle clamps (7). By pulling the ends of the belts more or less through these clamps (7) the belts can be made shorter or longer respectively. By varying the length of the abdominal belt (6) canting of the pelvis is possible from maximal lordosis to maximal cyphosis.

The position of the pelvical girdle (5) and the abdominal belt (6), which can be varied with regard to the transversal axis of both hips defines the sagging of the pelvis in its lower direction.

The pelvical girdle seizes at the pelvis directly and adapts its fixation. In this manner it is now possible to adjust the pelvis and the lumbar part of the spinal column which is the solution for a long-felt need in physiotherapy of spinal deflections and related diseases.

It is also possible to apply a treatment of traction from the head side of the table, which means that with this device the pelvis can be fastened and the thorax part of the body can be moved upward.

Specific techniques can be applied, such as symmetrical total lumbar traction as well as asymmetric traction in various positions depending on descriptions. The belts and girdles are made of inextensible canvas, clamps and rods are made of anticorrosive or galvanized steel that are covered where necessary. The thoracal fixation belt (1) and its widened part (2), the pelvical girdle (5) and the abdominal belt (6) are anatomically shaped since it is necessary to place the thoracal fixation belt (1) on the lowest thoracic aperture to hold back the thorax, so that the thoracolumbar transition is fixed against the table.

As a result of the comfortable fitting and the very slight physical charge the treatment of traction by means of the present system can be maintained in the statical position during 15 to 30 minutes.

The traction can also be applied intermittently, or oscillating, and either total or segmental.

It is possible to apply a servo-controlled servo-motor for an intermittent or continuous traction.

For this embodiment of the invention the traction rope (10) which is fastened in the middle of the connection rod (9) between the longitudinal traction belts (4) is connected with a pulley block and the motor, or directly with the controlled motor, and a measuring device or recorder can reproduce the traction force at this point which can be an important indication for the therapist to determine the further cycle of treatment.

If a pulley block is used the unit comprises two blocks and a not-extensible cord or rope (10).

One block is fastened in the middle of the steel connection rod (9) and the other block is fastened at the foot end of the frame of the table.

After about 15 minutes a maximal relief of tension of the lumbar structures is observed, whereafter the therapist can take over the manual treatment, by taking place within the sling of traction girdle (8), detaching the rope (10) and decrease the traction force very slowly and gradually.

I claim:

1. A device for the physiotherapeutical treatment of intervertebral disfigurement diseases by uni- or polydimensional traction at the lumbar part of the spinal column and the pelvis of humans, comprising a table with a thoracal fixation belt (1) having an anatomically shaped widened chest part (2), said belt is affixed around said table and around the patient by adjustment of an extension piece (3) of said belt (1), and with a traction part comprising a pelvical girdle (5) with an abdominal belt (6) that is affixed around the patients pelvis and abdomen respectively, said pelvical girdle (5) and said abdominal belt (6) being connected at each side with one of a pair of longitudinal traction belts (4), which extend towards the foot end of said table, and which are connected at said foot end by means of handle clamps (7) to a traction girdle (8), which can be slung around the therapist, standing at said foot end, said girdle (8) being connected to a connection rod (9), which has a traction rope (10) in the middle of a pulley block with a mechanical traction drive, wherein the patient is supported by means of an adjusting wedge that is positioned on the table and (11) laid under the body.

2. A device according to claim 1, comprising belts and girdles consisting of twill woven canvas material having fastening ends of tangle strings consisting of ribbons provided with hooks and eyes.

3. A device according to claim 1, wherein said traction rope (10) is connected with a pulley block for exercising a traction by hands.

4. A device according to claim 1, where said traction rope (10) is connected with a block which is driven by a servo-controlled servo-motor such that the traction can be controlled very slowly and can be kept during a number of minutes at an equal level.

5. A method for the physiotherapeutical treatment of intervertebral disfigurement diseases, comprising that upon the patient a chest part (2) of a thoracal fixation belt (1) is laid, the thoracal fixation belt (1) is laid underneath the table and the ends are fastened to each other by means of buckles, clasps or faster means with hooks and eyes, then that the pelvical girdle (5) is laid around the pelvis and the abdominal belt (6) is laid over the stomach, the longitudinal traction belts (4) being directed towards the foot end of the table, while the connection rod (9) is laid near the foot end of said table and traction is effected by means of a pulley block, which is attached in the middle of said connection rod (9).

6. A method according to claim 5, comprising that a servo-controlled electrical servo motor is attached at said connection rod (9) by means of a traction rope (10).

* * * * *